US00PP13346P2

(12) United States Plant Patent
van Rijn

(10) Patent No.: US PP13,346 P2
(45) Date of Patent: Dec. 10, 2002

(54) ANTHURIUM PLANT NAMED 'PINK GIANT'

(75) Inventor: Leonardus W. B. M. van Rijn, AM Schipluiden (NL)

(73) Assignee: Rijnplant B.V., Schipluiden (NL)

( * ) Notice: Subject to any disclaimer, the term of this patent is extended or adjusted under 35 U.S.C. 154(b) by 0 days.

(21) Appl. No.: 09/968,324

(22) Filed: Sep. 30, 2001

(51) Int. Cl.[7] ..... A01H 5/00
(52) U.S. Cl. ..... Plt./367

(58) Field of Search ..... Plt./367

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Anthurium plant named 'Pink Giant', characterized by its upright and somewhat outwardly spreading plant habit; freely clumping growth habit; large durable dark green leaves; large pink-colored spathes with lighter pink-colored spadices that are positioned above and beyond the foliage on strong and erect scapes; freely flowering habit; and good inflorescence longevity.

2 Drawing Sheets

BACKGROUND OF THE INVENTION

Botanical classification: *Anthurium andreanum.*

Variety denomination: 'Pink Giant'.

The present invention relates to a new and distinct cultivar of Anthurium plant, botanically known as *Anthurium andreanum*, and hereinafter referred to by the name 'Pink Giant'.

The new Anthurium is a product of a planned breeding program conducted by the Inventor in Schipluiden, The Netherlands. The objective of the program is to create and develop new freely clumping and freely flowering Anthurium cultivars with strong roots, dark green leaves, attractive spathe color, and good inflorescence longevity.

The new Anthurium originated from a cross by the Inventor on or about Jun. 24, 1997 of the Inventor's proprietary *Anthurium andreanum* selection code number 92-2 as the female, or seed, parent with the Inventor's proprietary *Anthurium andreanum* selection code number 93-03 as the male, or pollen, parent. The cultivar Pink Giant was discovered and selected by the Inventor as a plant within the progeny of the stated cross in a controlled environment in Schipluiden, The Netherlands in 1998.

Asexual propagation of the new cultivar by meristem culture in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Pink Giant. These characteristics in combination distinguish 'Pink Giant' as a new and distinct cultivar:

1. Upright and somewhat outwardly spreading plant habit.
2. Freely clumping growth habit.
3. Large durable dark green leaves.

4. Large pink-colored spathes with light pink-colored spadices that are positioned above and beyond the foliage on strong and erect scapes.
5. Freely flowering habit.
6. Good inflorescence longevity.

Plants of the new Anthurium can be compared to plants of the female parent, the selection 92-2. In side-by-side comparisons conducted in Schipluiden, The Netherlands, plants of the new Anthurium differed from plants of the selection 92-2 in the following characteristics:

1. Plants of the new Anthurium had broader leaves than plants of the selection 92-2.
2. Plants of the new Anthurium had larger and broader spathes than plants of the selection 92-2.
3. Plants of the new Anthuriums and plants of the selection 92-2 differed in spathe color.

Plants of the new Anthurium can be compared to plants of the male parent, the selection 93-03. In side-by-side comparisons conducted in Schipluiden, The Netherlands, plants of the new Anthurium differed from plants of the selection 93-03 in the following characteristics:

1. Plants of the new Anthurium had thicker and broader leaves than plants of the selection 93-03.
2. Plants of the new Anthurium had broader and smaller spathes than plants of the selection 93-03.

Plants of the new Anthurium can also be compared to plants of the cultivar Lisette, not patented. In side-by-side comparisons conducted in Schipluiden, The Netherlands, plants of the new Anthurium differed from plants of the cultivar Lisette in the following characteristics:

1. Plants of the new Anthurium had broader leaves than plants of the cultivar Lisette.
2. Plants of the new Anthurium had broader and larger spathes than plants of the cultivar Lisette.
3. Plants of the new Anthurium and the cultivar Lisette differed in spathe color.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type. Colors in the photographs may differ slightly from the color values cited in the detailed botanical description which accurately describe the colors of the new Anthurium.

The photograph at the top of the first sheet comprises a side perspective view of a typical flowering plant of the cultivar Pink Giant that was about three years old.

The photograph at the bottom of the first sheet comprises a close-up view of a typical inflorescence of 'Pink Giant'.

The photograph at the top of the second sheet comprises a close-up view of a typical inflorescence of 'Pink Giant'.

The photograph at the bottom of the second sheet comprises a close-up view of the upper surface of a typical mature leaf of 'Pink Giant'.

DETAILED BOTANICAL DESCRIPTION

In the following description, color references are made to The Royal Horticultural Society Colour Chart, 1995 edition, except where general terms of ordinary dictionary significance are used. The following observations and measurements describe three-year old plants grown in 17-cm containers in Schipluiden, The Netherlands, in a glass greenhouse with an average day temperature of 25° C. and an average night temperature of 19° C.

Botanical classification: *Anthurium andreanum* cultivar Pink Giant.

Parentage:

*Female parent.*—Inventor's proprietary *Anthurium andreanum* selection code number 92-2, not patented.

*Male parent.*—Inventor's proprietary *Anthurium andreanum* selection code number 93-03, not patented.

Propagation:

*Method.*—By meristem culture.

*Time to develop roots on a meristem-cultured plant.*—Summer: About 70 days at 24° C. Winter: About 84 days at 21° C.

*Root description.*—Strong fleshy roots.

Plant description:

*Plant shape.*—Upright and somewhat outwardly spreading plant habit, inverted triangle, symmetrical.

*Growth habit.*—Freely clumping, bushy and dense growth habit. Appropriate for 17 to 35-cm containers. Vigorous.

*Plant height.*—About 90 to 110 cm.

*Plant diameter or spread.*—About 95 cm.

*Crop time.*—About 10 months are usually required from planting of young plants to finished plants in a 17-cm container.

*Foliage description.*—Quantity per plant: About 80. Length: About 25 to 45 cm. Width: About 15 to 25 cm. Shape: Cordate. Apex: Apiculate. Base: Roughly auriculate; lobes not overlapping. Margin: Entire. Texture: Leather; glabrous. Venation pattern: Pinnate. Color: Young leaves, upper surface: Between 144A and 147A. Young leaves, lower surface: 146C. Mature leaves, upper surface: Darker than 147A. Mature leaves, lower surface: 146B. Venation, upper surface: 146A. Venation, lower surface: 145A. Petiole: Length: About 50 to 60 cm. Color: 144A. Geniculum length: About 3 to 5 cm. Geniculum color: 144A.

Inflorescence description:

*Inflorescence arrangement.*—Spathes with spadices held above and beyond the foliage. Flowering structures, arise from leaf axils. Freely and continuous flowering year-round; typically more than 25 inflorescences per plant at one time.

*Inflorescence longevity.*—Inflorescences last about six weeks under winter conditions and about three months under summer conditions; persistent.

*Spathe.*—Length: About 18 to 23 cm. Width: About 15 to 18 cm. Shape: Cordate. Apex: Aristate to mucronulate. Base: Auriculate; lobes not overlapping. Margin: Entire. Texture: Leathery; glabrous; slight blistering. Color: When opening, front and back surfaces: 144A; glossy. As spathes develop, spathes are green and pink. Fully developed, front surface: 50B; fading to lighter than 50B with subsequent development; glossy. Fully opened, back surface: 51B; glossy.

*Spadix.*—Length: About 12 to 14 cm. Diameter: About 1.3 cm. Shape: Columnar. Cross section: Rounded. Longitudinal axis: Erect. Color: Immature: 146B. Mature: 49C.

*Flowers.*—Quantity per spadix: Numerous, about 400. Shape: Rounded. Diameter: About 1 mm, maximum.

*Reproductive organs.*—Androecium: Pollen color: Close to 159B. Gynoecium: Stigma shape: Ovoid.

*Scape.*—Length: About 60 to 80 cm. Aspect: Strong and erect. Color: 144A.

*Seed/fruit.*—Seed/fruit development on plants of the new Anthurium has not been observed to date.

Disease/pest resistance: Under commercial conditions, plants of the new Anthurium have not been observed to be resistant to pathogens or pests common to Anthurium.

It is claimed:

1. A new and distinct cultivar of Anthurium plant named 'Pink Giant', as illustrated and described.

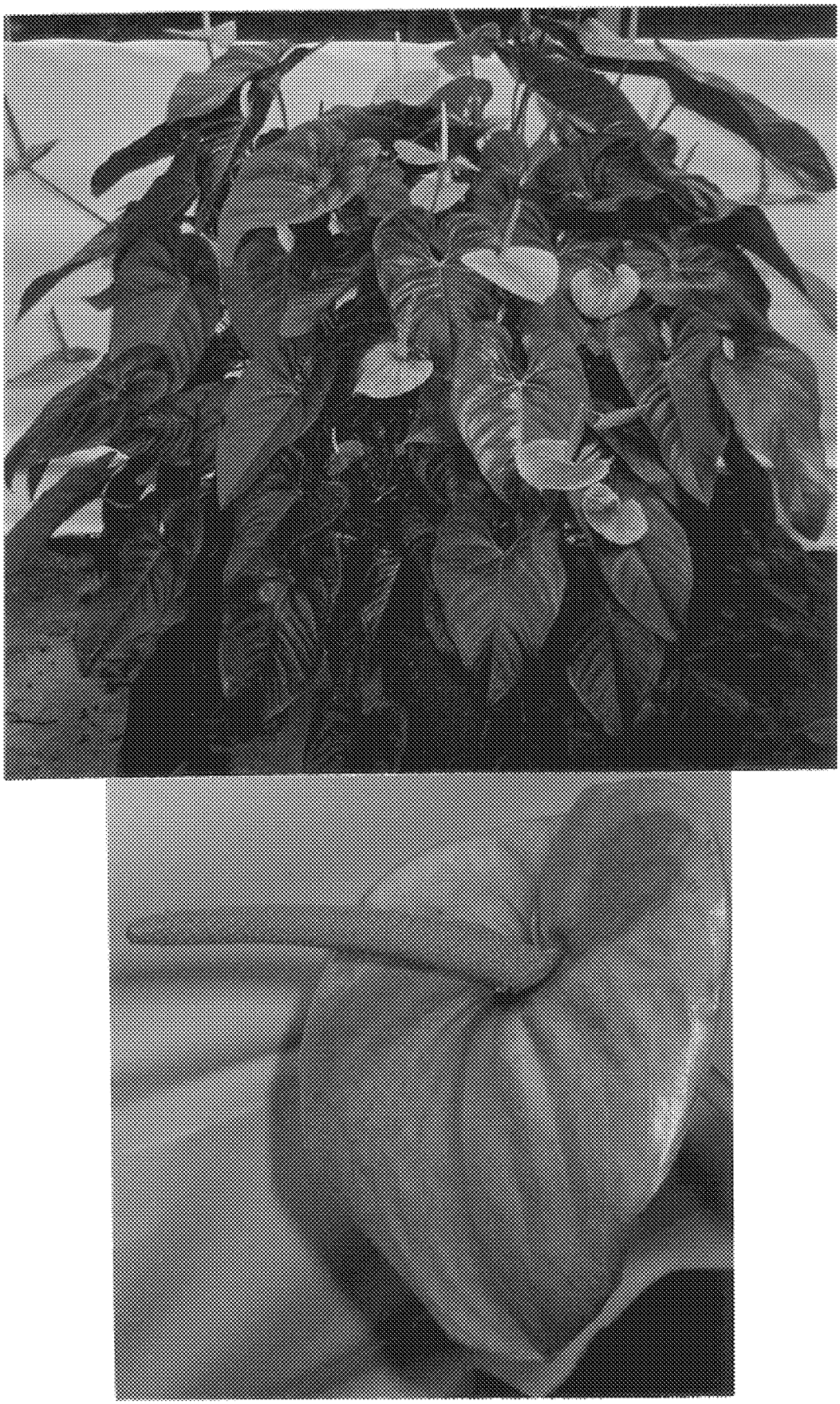

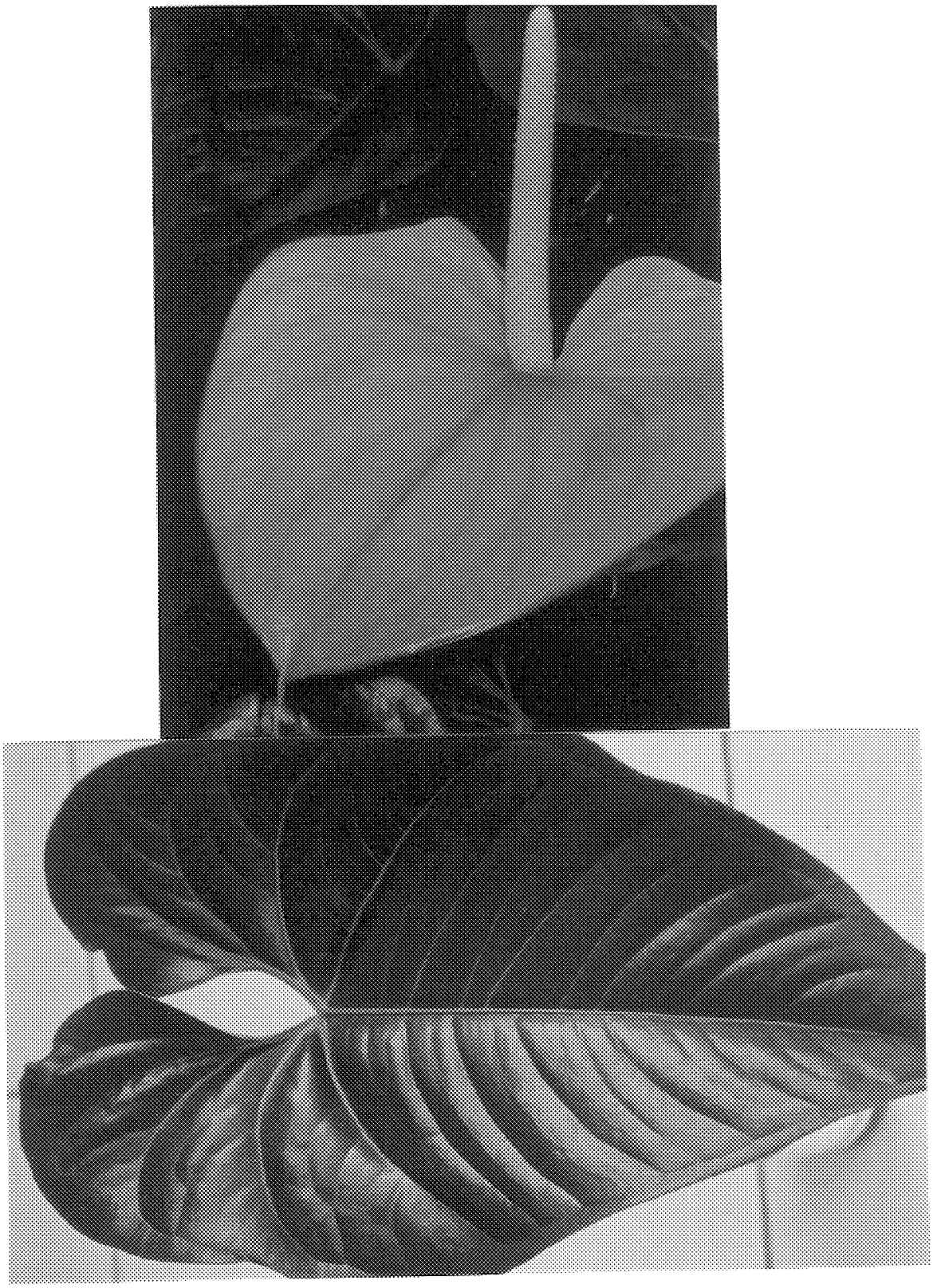

* * * * *